(12) United States Patent
Kajitani et al.

(10) Patent No.: US 6,980,301 B2
(45) Date of Patent: Dec. 27, 2005

(54) METHOD AND APPARATUS FOR THREE-DIMENSIONAL SURFACE MORPHOMETRY

(75) Inventors: Tetsuya Kajitani, Tokyo (JP); Yoshitake Yamaoka, Saitama (JP); Katsunori Shimomura, 3-1-4-203, Nagayama, Tama-shi, Tokyo 206-0025 (JP)

(73) Assignees: Cubic Co., LTD, Tokyo (JP); Isohachi Okamura, Tokyo (JP); Katsunori Shimomura, Tokyo (JP)

( * ) Notice: Subject to any disclaimer, the term of this patent is extended or adjusted under 35 U.S.C. 154(b) by 334 days.

(21) Appl. No.: 10/202,677

(22) Filed: Jul. 25, 2002

(65) Prior Publication Data

US 2004/0017886 A1 Jan. 29, 2004

(51) Int. Cl.⁷ .............................................. G01B 11/24
(52) U.S. Cl. ....................... 356/601; 382/154; 345/474
(58) Field of Search .............................. 356/601–612; 382/154; 348/42, 47; 345/474

(56) References Cited

U.S. PATENT DOCUMENTS

| | | | | |
|---|---|---|---|---|
| 6,084,979 A | * | 7/2000 | Kanade et al. ............... | 382/154 |
| 6,373,487 B1 | * | 4/2002 | Culbertson et al. .......... | 382/132 |
| 6,674,461 B1 | * | 1/2004 | Klapman ...................... | 348/42 |

FOREIGN PATENT DOCUMENTS

| | | |
|---|---|---|
| JP | 03-076122 | 12/1991 |
| JP | 05-071882 | 10/1993 |
| JP | 06-167455 | 6/1994 |
| JP | 06-065964 | 8/1994 |
| JP | 06-331329 | 12/1994 |
| JP | 07-139922 | 6/1995 |
| JP | 09-257437 | 10/1997 |
| JP | 10-122850 | 5/1998 |
| JP | 10-267624 | 10/1998 |
| JP | 11-101623 | 4/1999 |
| JP | 2001-264035 | 9/2001 |

* cited by examiner

Primary Examiner—Layla G. Lauchman
(74) Attorney, Agent, or Firm—Finnegan Henderson Farabow Garrett & Dunner L.L.P.

(57) ABSTRACT

The present invention provides a method and apparatus for non-contacting morphomtry of three-dimensional surface of an object such as a human body in a shorter time period and with higher precision, wherein the present non-contacting morphometry of three-dimensional surface of an object involves a plurality of measuring video heads, $A_i$, $B_i$, $C_i$ and $D_i$ and a controlling unit for controlling the measuring time of the measuring heads and for processing and storing the obtained data from the measurements. The present method comprises the steps of: placing the object to be measured so that one axis thereof lies along and with an imaginary central axis; placing the object to be measured so that the measuring heads are arranged on each of n (n≧1) planes intersecting the imaginary central axis where the optical axis of each measuring head faces the imaginary central axis and each annular slice of the surface of the object is covered by the sight fields of the m (m≧3) measuring heads; operating simultaneously one group of a plurality of measuring video heads, the sight field of each of which does not substantially overlap with the sight field of the other in the group, and thereafter, operating other group of a plurality of measuring video heads, the sight field of each of which does not substantially overlap with the sight field of the other in the group. The n×m sets of data thus obtained in the foregoing steps are processed to obtain three-dimensional data.

10 Claims, 8 Drawing Sheets

METHOD AND APPARATUS FOR THREE-DIMENSIONAL SURFACE MORPHOMETRY

BACKGROUND OF THE INVENTION

The present invention relates to a method and apparatus for morphometry of three-dimensional surface of an object such as a human body with higher precision and efficiency.

There is a strong need for precise, efficient measuring apparatus to determine the morphometry of the three-dimensional surface of an object such as a human body, in the medical and apparel fields. Morphometry refers to the measurement, study and analysis of size, shape, and/or the structure of objects, and may also include measurement of the geometrical interrelationships between objects. Three dimensional morphometry, in particular, refers to measurement, capture and study of the above parameters for three-dimensional objects in the real world. Three-dimensional morphometry may include the generation of three-dimensional models that may be analyzed and transformed using image processing techniques. Measurement and utilization of data of a complex form, such as a human body, requires the entire body to be completely scanned and further that the body be kept still during the measurement. Thus, under such conditions, it is critical that the measuring apparatus be able to measure as fast as possible. A number of proposals have been made concerning the morphometry of the three-dimensional surface of a still object, such as a human body. In the Japanese Patent Laid-Open Publication No. Hei10-122850, an apparatus for three-dimensional morphometry using PSD, is disclosed. The disclosed apparatus has a complex mechanism, requiring a moving frame, a plurality of sensors disposed facing each other on each of the two opposite side walls of the frame for scanning and operating light beams horizontally for measuring the distance to the human body, and a driving mechanism for moving the frame. In addition, the application notes the difficulty of having a measuring time short enough to avoid the effect of movement caused due to physiological needs of the human body.

SUMMARY OF THE INVENTION

In the present invention, the following requirement goals were set for the present morphometry of a human body:
1. measuring range (height): 900 mm to 2,000 mm;
2. measuring range (diameter): 600 mm to 1,500 mm
3. measuring time (entire body): 1 second;
4. acceptable tolerance of measured value (absolute tolerance): 1 mm (preferably, 0.2 mm);
5. processing time of the measured data: 30 second.

One of the objects of the present invention is to provide a method and apparatus that enables to solve each of the above problems, wherein the method and apparatus measures a three-dimensional surface of an object, such as a human body, with higher precision and efficiency.

To achieve the object and in accordance with the purpose of the invention, as embodied and broadly described herein, the present invention comprises a non-contact type apparatus for and a method of three-dimensional morphometry using a plurality of measuring video heads disposed facing the object to be measured. The apparatus includes a controlling unit, which controls the measuring time period of each of the measuring video heads and processes and stores the measured data. The method further comprises the steps of:

placing in a space the object to be measured: so that one axis of the object to be measured lies along and with an imaginary central axis of the space; further the measuring heads are arranged on each of n (n≧1) planes intersecting the imaginary central axis where the optical axis of each measuring head lies on one of the n planes and is substantially perpendicular to and faces the imaginary central axis so that each annular slice of the surface of the object is covered by the sight fields of the m (m≧3) measuring heads; and operating simultaneously one group of a plurality of measuring video heads, the sight field of each of which does not substantially overlap with the sight field of the other in the group, and thereafter, operating other group of a plurality of measuring video heads, the sight field of each of which does not substantially overlap with the sight field of the other in the group and processing the n×m sets of data obtained in the foregoing steps thereby to obtain three-dimensional data.

The present invention also provides an apparatus embodying the foregoing method of three-dimensional morphometry, the apparatus comprising: a space for placing an object to be measured so that one axis of the object lies along and with an imaginary central axis of the space; a plurality of measuring heads being disposed outside of the space for each to capture an image of a portion of a surface of the object, where the portions of the surface of the object may substantially overlap with each other; and a controlling unit for obtaining three-dimensional data by operating a group of a plurality of measuring heads, the sight field of each of which does not substantially overlap with that of other measuring heads in the group. Each group of measuring heads is operated to retrieve sets of data, which are then processed.

BRIEF DESCRIPTION OF THE DRAWINGS

The accompanying drawings, which are incorporated herein and constitute a part of this specification for illustrative purposes, illustrate embodiments of the invention and, together with the description, serve to explain some of the objects, advantages and principles of the invention.

DETAILED DESCRIPTION OF

Figure 1:
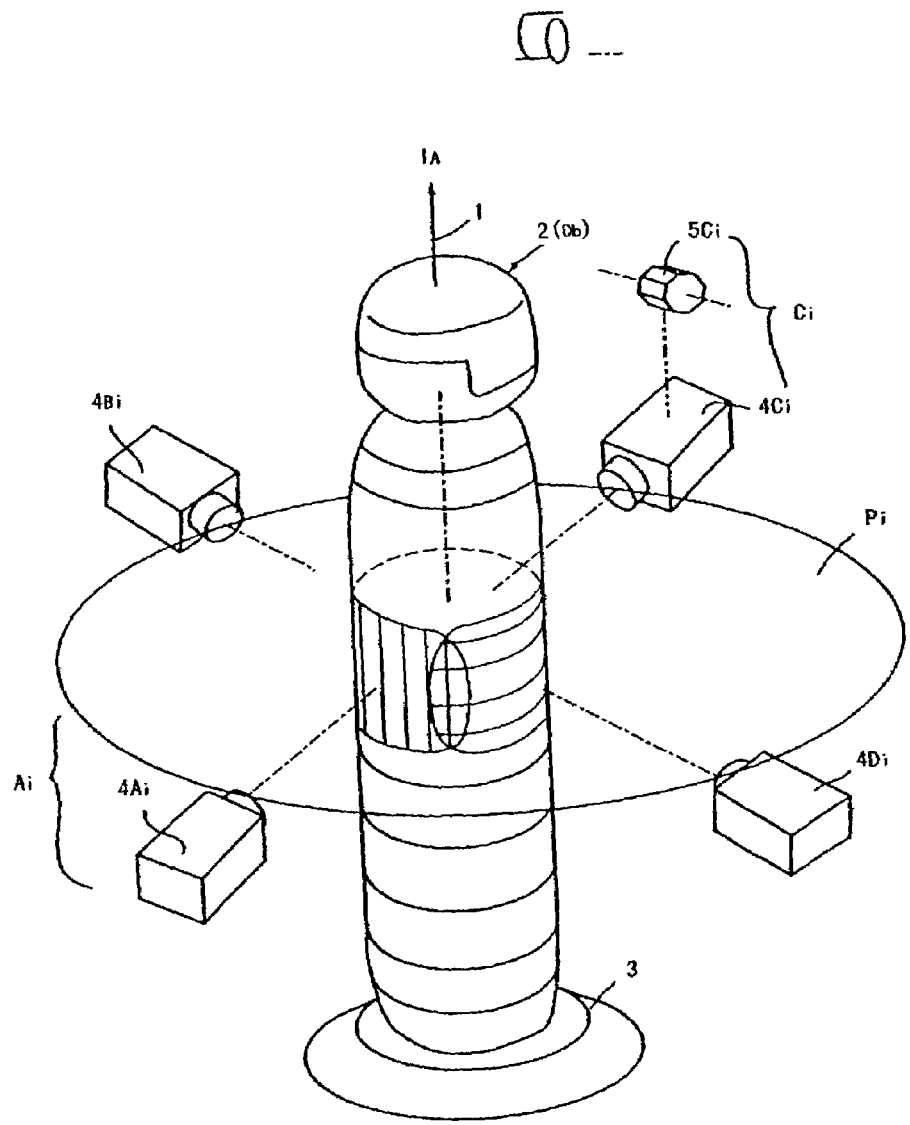
FIG. 1 is a schematic perspective view illustrating principles of a method and apparatus for morphometry of the three dimensional surface of an object in accordance with embodiments of the present invention.
Figure 5:
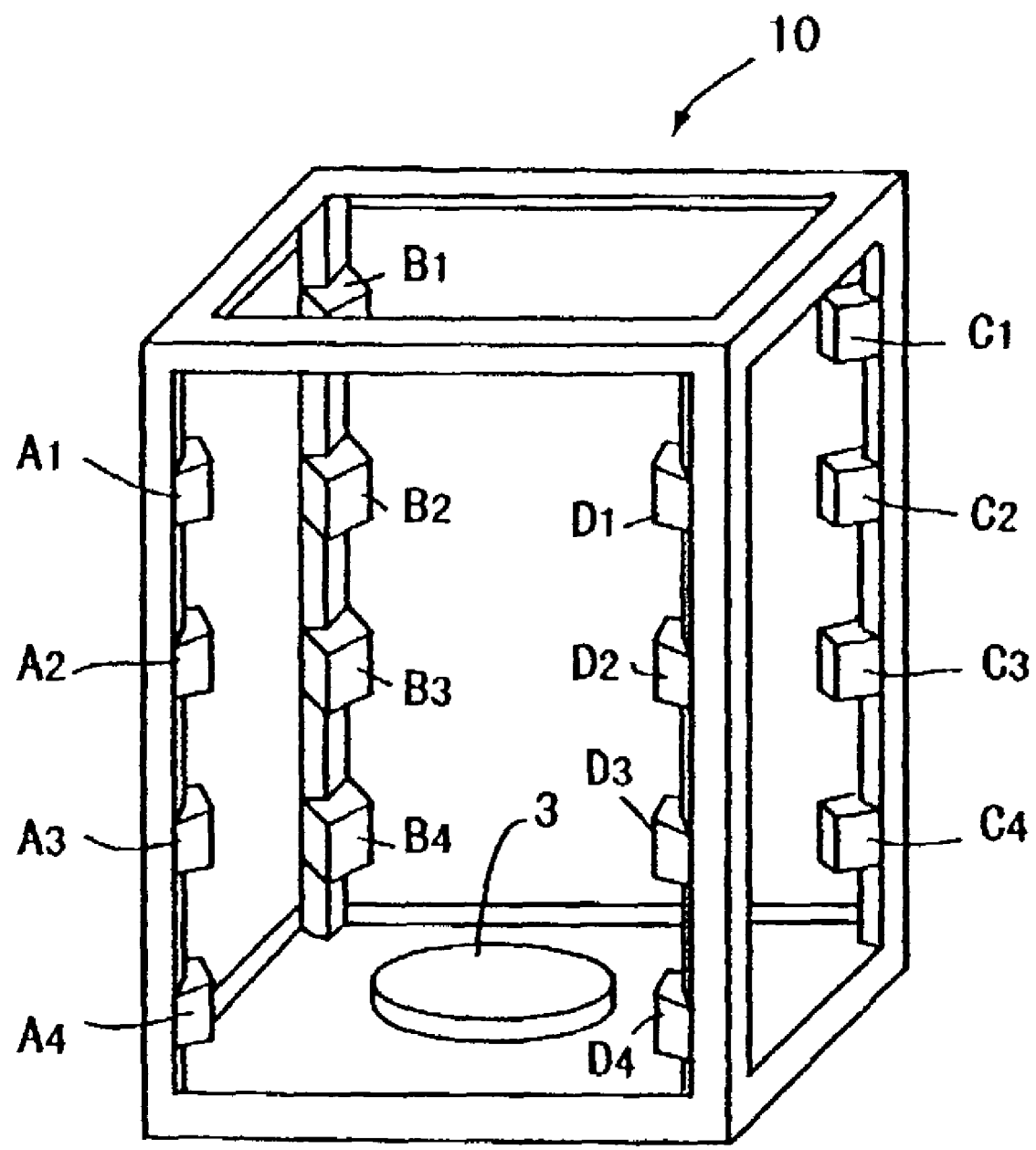
FIG. 5 is a perspective view illustrating the arrangement of measuring heads with respect to the image capturing frame according to embodiments of a method and apparatus for morphometry of three dimensional surfaces, consistent with the present invention.

FIG. 1, shows a schematic perspective diagram illustrating principles of a method and apparatus for morphometry of three-dimensional surface of an object in accordance with embodiments of the present invention. FIG. 5 shows a perspective diagram of the arrangement of measuring heads with respect to an image capturing frame according to some embodiments of a method and apparatus for morphometry of the three-dimensional surface of an object, in accordance with the present invention. The schematic diagram of FIG. 1 illustrates an arrangement where an object (Ob) 2, such as a standing human body, is placed on a base 3 of an image capturing frame, as shown in FIG. 5, with an imaginary central axis (IA) 1 being in the center thereof, with respect to CCD cameras of a given level.

Figure 2:
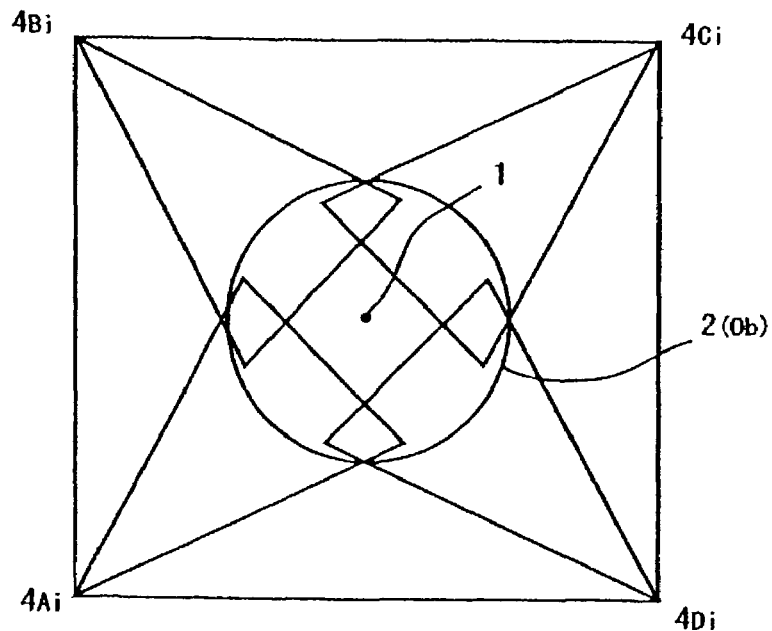
FIG. 2 is a schematic plan view illustrating the relationship between the overlap of sight fields of cameras and the object to be measured according to some embodiments of the invention.

CCD cameras, $4_{Ai}$, $4_{Bi}$, $4_{Ci}$, $4_{Di}$, are each arranged such that each optical axis lies on the plane $P_i$ which intersects the imaginary central axis (IA) of FIG. 1, and the sight fields of four CCD measuring heads cover the whole annular slice of the object (Ob) 2. FIG. 2 illustrates a plan view showing the overlapping sight fields of cameras $4_{Ai}$, $4_{Bi}$, $4_{Ci}$, $4_{Di}$ and their relationship with the object to be measured (Ob).

Figure 3:
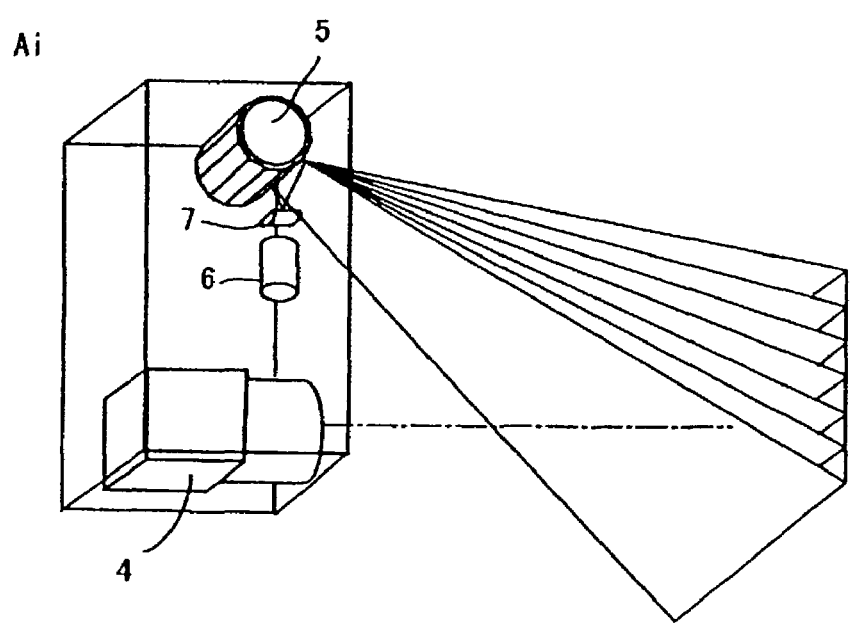
FIG. 3 is a schematic diagram illustrating the arrangement of measuring heads and the principle of operation of the optics, according to some embodiments of the invention.
Figure 4:
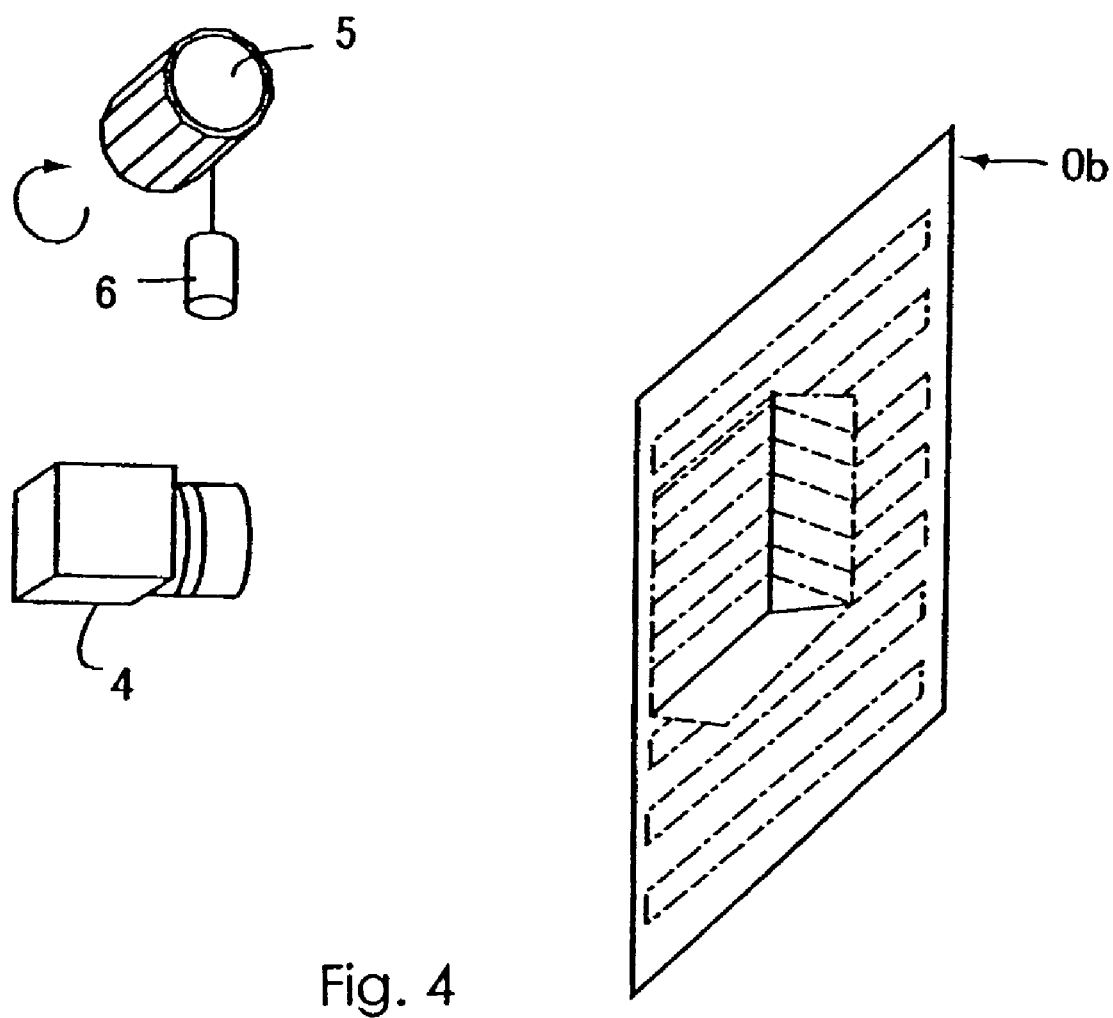
FIG. 4 is a schematic diagram illustrating the arrangement of measuring heads and the projecting pattern according to some embodiments of the invention.

FIG. 3 shows the arrangement of the measuring heads and functional principles of the operation of optical components, according to embodiments of the invention. FIG. 4 shows a schematic diagram of the arrangement of the measuring heads and the image capturing pattern according to embodiments of the invention. Measuring heads $A_i$, $B_i$, $C_i$, $D_i$ each incorporate a CCD camera 4, a polygon mirror 5, a laser light source 6 and a cylindrical lens 7. CCD camera 4 and the polygon mirror 5 are placed at a predetermined distance (at a base line distance) from each other. The light beam emitted from the laser 6, which is a time-domain modulated light source, is focused on the polygon mirror 5 by the cylindrical lens 7 to be scanned by the rotation of the polygon mirror 5 and thereby forming on the object Ob a moiré pattern corresponding to the surface configuration of the object Ob. The pattern is captured by the CCD camera 4.

Figure 6:
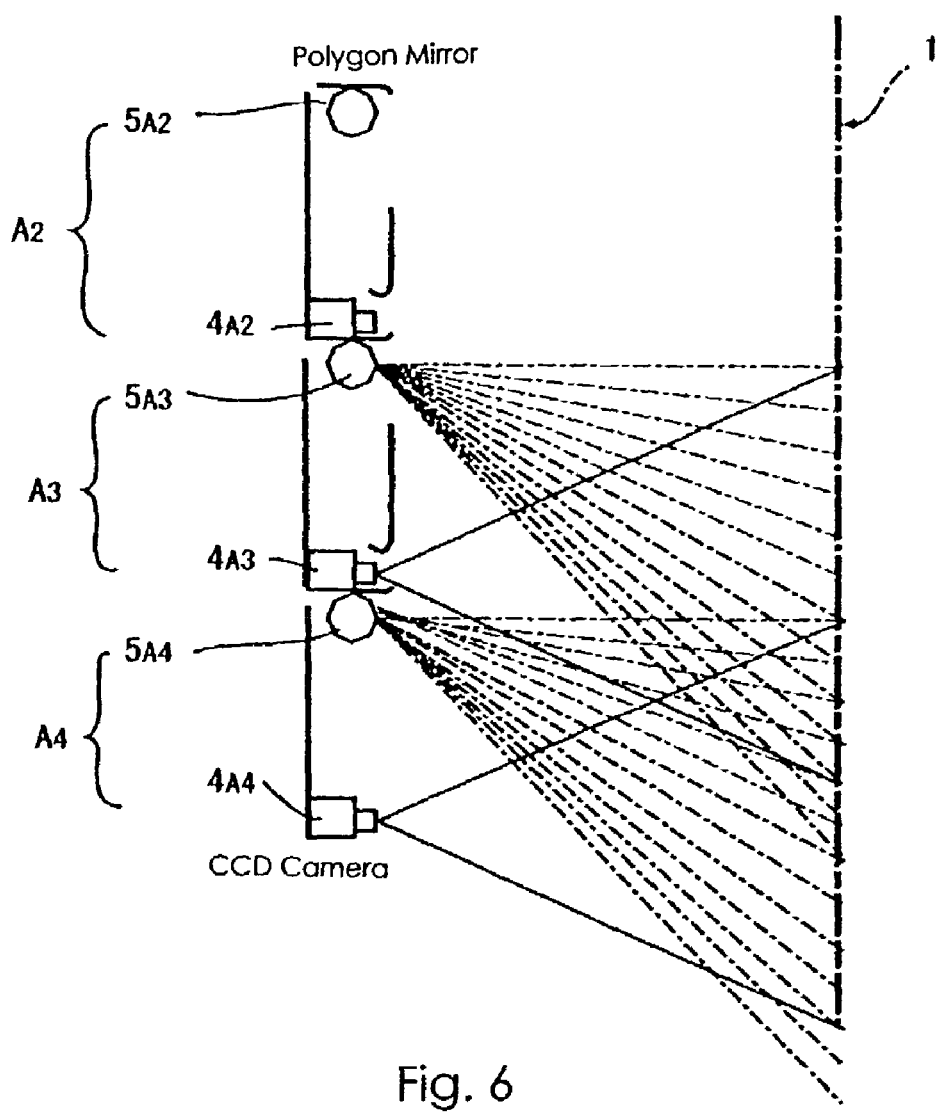
FIG. 6 is a schematic diagram illustrating the arrangement of video heads used for measurements, along the vertical direction and showing the overlap of sight fields in accordance with some embodiments of the invention.

FIG. 6 is a schematic diagram illustrating an arrangement, of the measuring video heads in the height direction, and showing the overlap of sight fields according to embodiments of the present invention. In FIG. 6, only the measuring heads $A_2$, $A_3$, $A_4$ of FIG. 5 are shown for simplicity. For example, the measuring head $A_3$ captures the image of the surface of the object (not shown) scanned by the polygon mirror $5_{A3}$.

Figure 7:
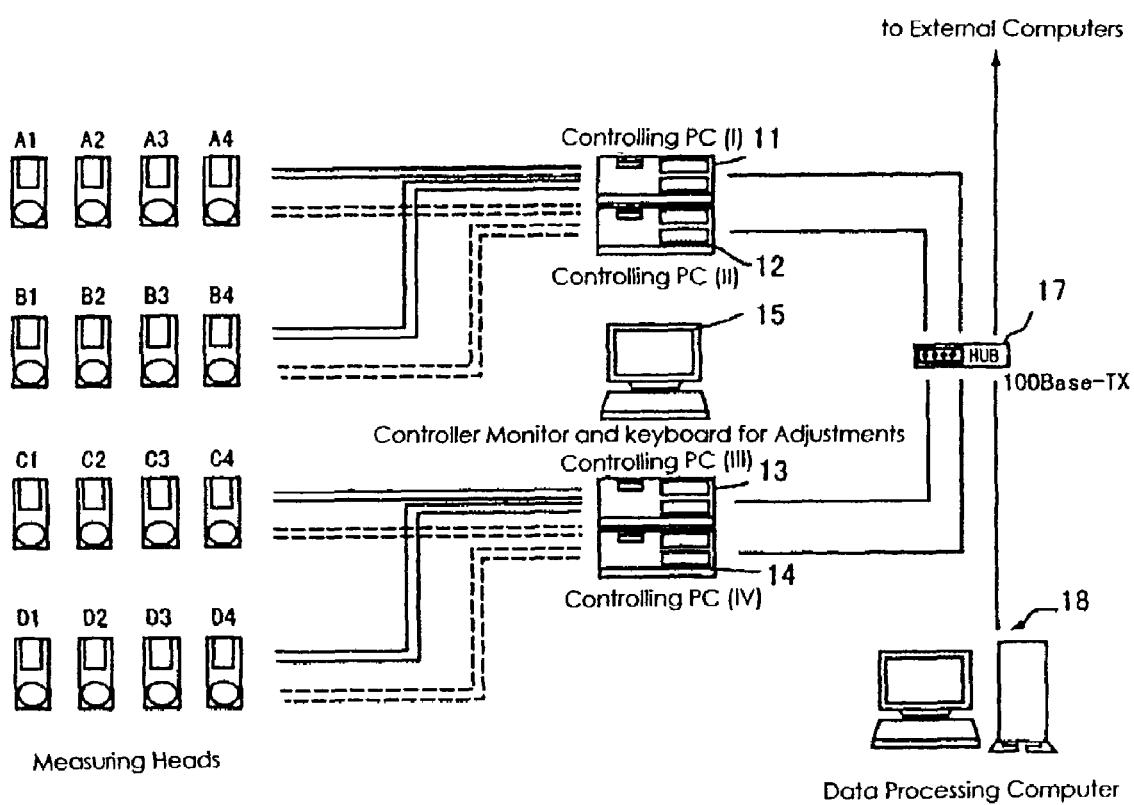
FIG. 7 is a schematic block diagram illustrating an exemplary system and apparatus for morphometry in accordance with the present invention.

FIG. 7 is a block diagram of a system and apparatus for the morphometry of three-dimensional surfaces, according to embodiments of the present invention. In some embodiments, a total of 16 heads may be used with 4 heads on each of the 4 rows. Measuring heads $A_1$, $A_2$, $A_3$, $A_4$ may be arranged in a line as shown in FIG. 5. Measuring heads $B_1$ through $B_4$, $C_1$ through $C_4$, $D_1$ through $D_4$ are also arranged in a similar manner. Controlling personal computers (PCs) PC (I) 11 and PC (II) 12 process the output from measuring heads in rows A and B, and a controlling PC's (III) 13 and PC (IV) 14 process the output from measuring heads in rows C and D. The output data from each of the controlling PCs 11 through 14 are processed by a data processing personal computer 18. The data, after being processed, are delivered to an external computer via a hub 17.

Figure 8:
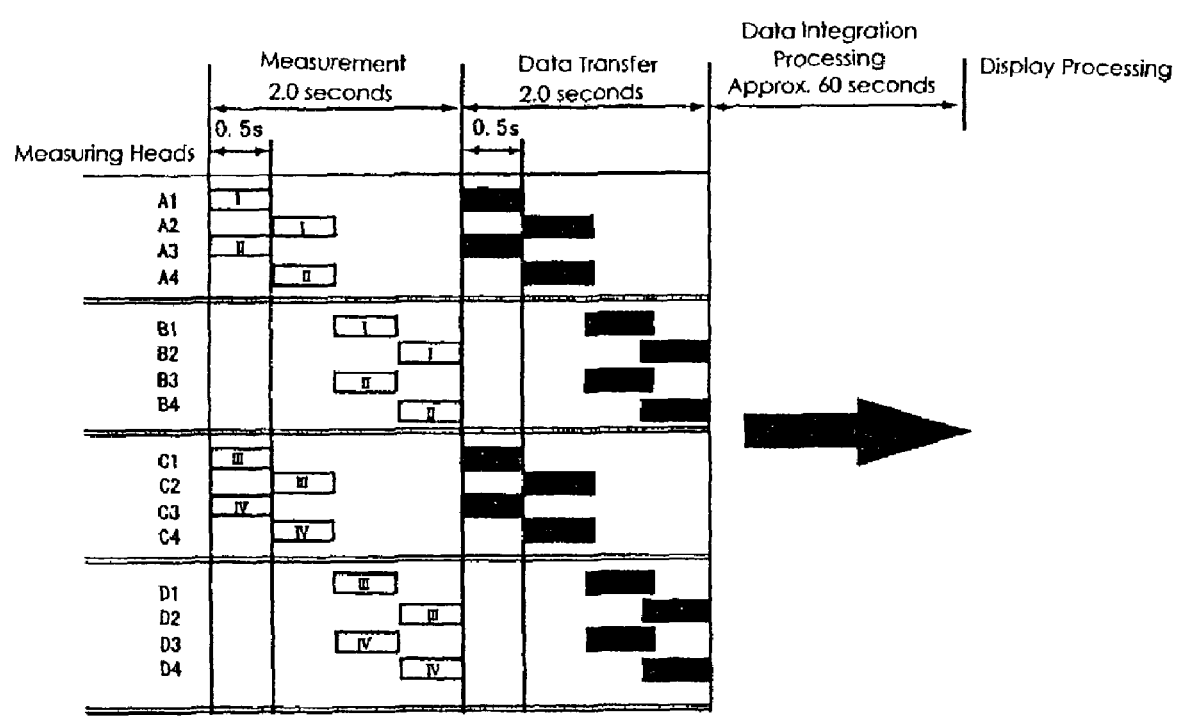
FIG. 8 illustrates a sequence of measurements, data transfer, and data processing of an apparatus for morphometry in accordance with embodiments of the present invention.

FIG. 8 is a sequence chart of the measurement, data transfer, and data processing according to some embodiments of an apparatus for morphometry of the three-dimensional surface of an object. In some embodiments, the measuring heads are grouped into subsets, and each subset is operated in a sequence of successive time segments. For example, in some systems according to embodiments of the present invention, 2.0 seconds may be set for the scheduled measuring time period for capturing data and preprocessing data, 2.0 seconds for the data transfer and 60 seconds for the integration of data. In some embodiments, during the first 0.5 seconds, each of the measuring heads $A_1$, $A_3$, $C_1$ and $C_3$ is operated. In some embodiments, during the first 0.5 second time period, measuring heads $A_2$, $A_4$, $C_2$, $C_4$, $B_1$, $B_2$, $B_3$, $B_4$, $D_1$, $D_2$, $D_3$, and $D_4$, each of which has an overlapping sight field with one of the foregoing measuring heads, are not operated.

In some embodiments, during the next 0.5 seconds (corresponding to within 0.5 to 1.0 seconds of commencing the morphometry process), the measuring heads $A_2$, $A_4$, $C_2$ and $C_4$ are operated. In some embodiments, during this subsequent 0.5 second period, the measuring heads $A_1$, $A_3$, $C_1$, $C_3$, $B_1$, $B_2$, $B_3$, $B_4$, $D_1$, $D_2$, $D_3$, and $D_4$, each of which has an overlapping sight field with one of the foregoing measuring heads, are not operated. In some embodiments during the next 0.5 seconds (corresponding to within 1.0 to 1.5 seconds of commencing the morphometry process), each of the measuring heads $B_1$, $B_3$, $D_1$ and $D_3$ is operated. In some embodiments, during this 1.0 to 1.5 second time period, measuring heads $B_2$, $B_4$, $D_2$, $D_4$, $A_1$, $A_2$, $A_3$, $A_4$, $C_1$, $C_2$, $C_3$, and $C_4$, each of which has an overlapping sight field with one of the foregoing measuring heads, are not operated.

In some embodiments, during the next 0.5 seconds (corresponding to within 1.5 to 2 seconds of commencing the morphometry process), each of the measuring heads $B_2$, $B_4$, $D_2$ and $D_4$ is operated. In some embodiments, during this 1.5 to 2 second time period, measuring heads $B_1$, $B_3$, $D_1$, $D_3$, $A_1$, $A_2$, $A_3$, $A_4$, $C_1$, $C_2$, $C_3$, and $C_4$, each of which has an overlapping sight field with one of the foregoing measuring heads, are not operated. In some embodiments, obtained by the measuring heads are then subjected to a preprocessing, such as for example, noise elimination and filtering) in the controlling PCs (I, II, III, IV) 11, 12, 13, 14 and transferred to data processing personal computer 18. In some embodiments, the data transfer may be performed using TCP/IP protocols, or other suitable data transfer protocols or mechanisms. In some embodiments, the computation of coordinates and the data integration processing may be performed in data processing personal computer 18.

Figure 9:
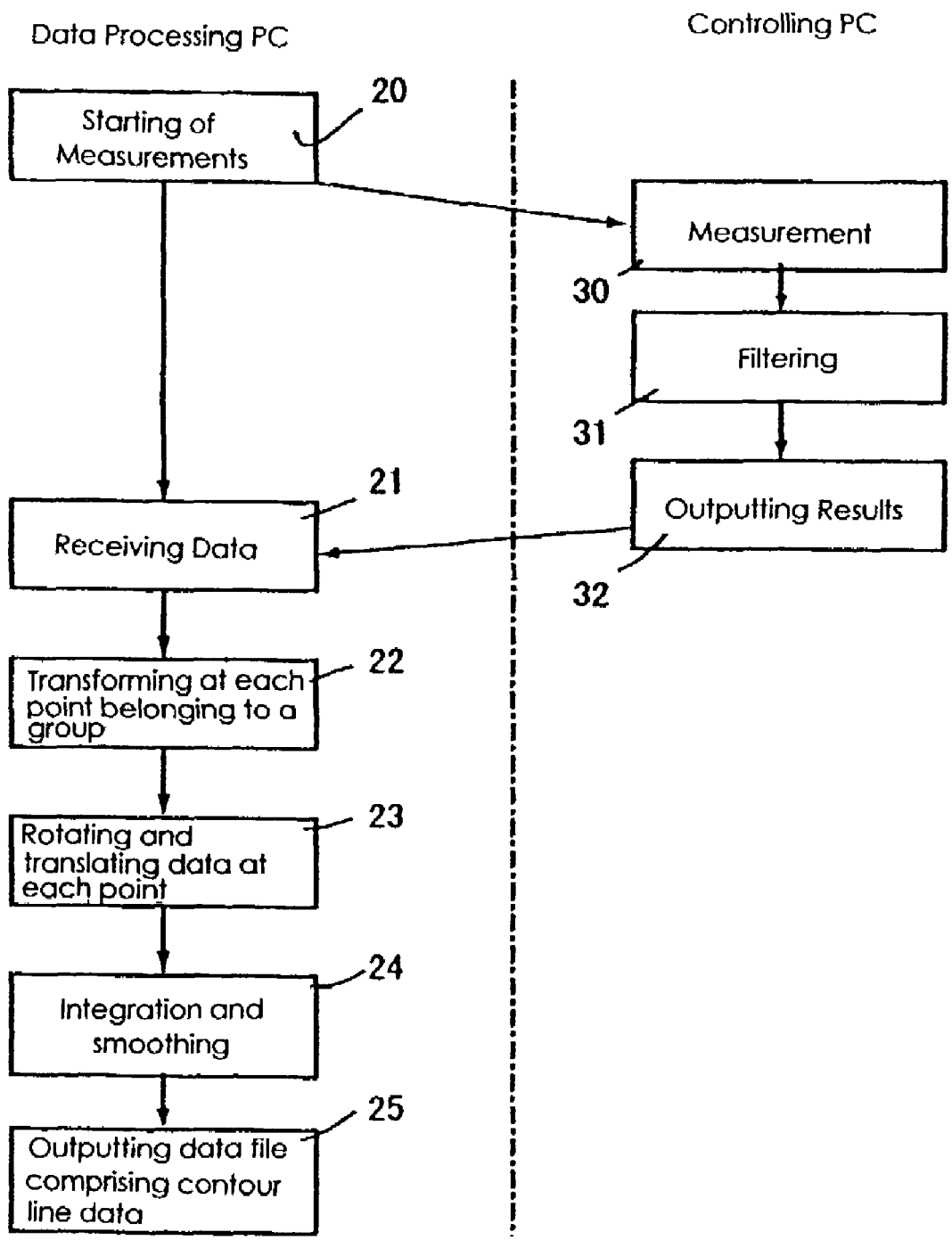
FIG. 9 illustrates a flowchart of measurements, data transfer, and data processing of an apparatus for morphometry in accordance with embodiments of the present invention.

FIG. 9 shows an exemplary flow chart of the measurement, data transfer, and data processing in some embodiments of an apparatus for morphometry of the three-dimensional surface of an object in accordance with the present invention. The flow chart illustrates the flow of process starting with the measurement up to the output of a final output data file.

In some embodiments, the exemplary process flow may be distributed among the computers as follows:

In step 20, the data processing PC directs the controlling personal computer (hereinafter, "controlling PC") to start the measurement. Next, in In step 30, the controlling PC instructs the measuring head to start the measurement.

In step 31, the controlling PC performs preprocessing, such as for example, filtering, on the data captured by the measuring head.

In step 32, the controlling PC outputs and delivers the preprocessed data output to the data processing PC.

In step 21, the data processing PC receives the preprocessed data from the controlling PC.

In step 22, the data processing PC performs a transformation operation on the data at each point belonging to a group.

In step 23, the data processing PC performs rotation and translation operations on the data at each point.

In step 24, the data processing PC performs integration and smoothing operation on the data.

In step 25, the data processing PC outputs a data rile comprising contour line data.

As can be seen from the description above, a method and apparatus for morphometry of the three-dimensional surface of an object, in accordance with the present invention facilitates the capture and processing of three-dimensional data of an object such as a human body. In some embodiments, data may be captured within a very short time period of 2.0 seconds, and the data thus obtained may be transformed to a three-dimensional representation, which can then be immediately output. It should be appreciated by those skilled in the art that the disclosed embodiment provides a complete set of solutions for the quantitative problems and objects cited above. Some embodiments of the present invention make it possible to build a database of three-dimensional data of a human body from captured data. In some embodiments, databases may be used to store captured data. In some embodiments, general purpose or other types of computers including special purpose computing apparatus may be used to perform the functions of the exemplary personal computers described above. It should be understood that the present invention is not to be limited to the description and exemplary embodiments described above and may be modified within the scope of the technical concepts described above as well as the accompanying claims. Other embodiments of the invention will be apparent to those skilled in the art from consideration of the specification and practice of the embodiments of the invention disclosed herein. It is intended that the specification and examples be considered as exemplary only, with a true scope and spirit of the invention being indicated by the following claims. As such, the invention is limited only by the following claims.

What is claimed is:

1. A method of non-contacting morphometry of three-dimensional surface of an object having a plurality of measuring video heads disposed facing the object to be measured and a controlling unit for controlling the measuring time period for each of m measuring video heads and for processing and storing the measured data, comprising the steps of:

placing the object to be measured so that one axis thereof lies along and with an imaginary central axis;

placing the object to be measured so that the measuring heads are arranged on each of n (n≧1) planes intersecting the imaginary central axis where the optical axis of each measuring head faces the imaginary central axis and each annular slice of the surface of the object is covered by the sight fields of the m (m≧3) measuring heads;

operating simultaneously one group of a plurality of measuring video heads, the sight field of each of which does not substantially overlap with the sight field of the others in the group, and thereafter, operating another group of a plurality of measuring video heads, the sight field of each of which does not substantially overlap with the sight field of the others in the group; and processing the n×m sets of data obtained in the foregoing steps and thereby to obtain three-dimensional data.

2. An apparatus of morphometry of three-dimensional surface of an object, comprising:

a space for placing an object to be measured so that one axis thereof lies along an imaginary central axis;

a plurality of measuring heads, arranged on each of n (n>1) planes intersecting the imaginary central axis, being disposed outside of the space for each to capture an image of a portion of a surface of the object while the portion may overlap with each other; and a controlling unit for obtaining three-dimensional data in real-time by operating a group of a plurality of measuring heads, the sight field of each of which does not substantially overlap with that of other measuring heads in the group, and thereafter, operating another group of a plurality of measuring heads, the sight field of each of which does not substantially overlap with that of other measuring heads in the group, and thereby concurrently processing a plurality of sets of data obtained by the operations.

3. A method for three-dimensional surface morphometry using a plurality of measuring heads with the optical axis of each measuring head facing an imaginary central axis comprising:

placing an object to be measured so that one axis lies along the imaginary central axis;

selecting groups of m (m≧3) measuring heads arranged on n (n≧1) planes intersecting the imaginary central axis and such that the sight field of each of the measuring heads in a group does not substantially overlap with the sight field of other measuring heads in the group and so that each annular slice of the surface of the object is covered by the sight fields of the measuring heads; and taking morphometric measurements of the object by operating each group of measuring heads in sequence; and processing the n×m sets of data obtained to yield three-dimensional image data.

4. The method of claim 3, wherein taking morphometric measurements of the object by operating each group of measuring heads in sequence further comprises controlling the time period that each group of measuring heads is operated.

5. The method of claim 3, wherein taking morphometric measurements of the object by operating each group of measuring heads in sequence and processing the n×m sets of data obtained in the foregoing steps and thereby to obtain three-dimensional data is performed using a control unit.

6. The method of claim 5, wherein the control unit is a computer.

7. The method of claim 3, wherein taking morphometric measurements of the object by operating each group of measuring heads in sequence is performed using a controlling computer and processing the n×m sets of data obtained to yield three-dimensional image data is performed using a data processing computer.

8. The method of claim 7, wherein data is exchanged between the control computer and the data processing computer using standard network protocols.

9. The method of claim 8, where the standard network protocol is the TCP/IP protocol.

10. The method of claim 3, wherein processing the n×m sets of data obtained to yield three-dimensional image data further comprises one or more of the steps of:

transforming the data measured by each group;
   rotating and translating the data;
   performing integration and smoothing of the of data; and
   outputting the data in a contour-line format to a data file.

* * * * *